United States Patent [19]

Steinmann et al.

[11] Patent Number: 5,599,651
[45] Date of Patent: Feb. 4, 1997

[54] (CYCLO)ALIPHATIC EPOXY COMPOUNDS

[75] Inventors: Bettina Steinmann, Praroman; Jean-Pierre Wolf, Courtaman; Adrian Schulthess, Tentlingen; Max Hunziker, Düdingen, all of Switzerland

[73] Assignee: Ciba-Geigy Corporation, Tarrytown, N.Y.

[21] Appl. No.: 517,888

[22] Filed: Aug. 21, 1995

Related U.S. Application Data

[62] Division of Ser. No. 169,938, Dec. 20, 1993, Pat. No. 5,468,886.

[30] Foreign Application Priority Data

Dec. 23, 1992 [CH] Switzerland ............... 3943/92

[51] Int. Cl.$^6$ ............... G03L 5/00; C07D 303/38
[52] U.S. Cl. .............. 430/280.1; 430/269; 522/170; 549/549
[58] Field of Search ............... 430/280.1, 269; 522/170; 549/549

[56] References Cited

U.S. PATENT DOCUMENTS

| | | | |
|---|---|---|---|
| 4,100,141 | 7/1978 | O'Sullivan | 526/301 |
| 4,565,859 | 1/1986 | Murai et al. | 549/554 |
| 4,895,873 | 1/1990 | Schäfer | 514/557 |
| 4,929,402 | 5/1990 | Hull | 264/22 |
| 5,218,074 | 6/1993 | Nordmann et al. | 549/549 |
| 5,326,827 | 7/1994 | Aoki et al. | 525/337 |

FOREIGN PATENT DOCUMENTS

| | | |
|---|---|---|
| 0171069 | 2/1986 | European Pat. Off. . |
| 0282634 | 9/1988 | European Pat. Off. . |
| 0360869 | 4/1990 | European Pat. Off. . |
| 0485990 | 5/1992 | European Pat. Off. . |
| 4232213 | 4/1993 | Germany . |
| 0788531 | 1/1958 | United Kingdom . |

OTHER PUBLICATIONS

Rev. Sci. Instrum. 52(11), Nov. 1981 pp. 1770–1773.
Chem. Abstr. vol. 60 No. 12, 14473d, Hasatani et al Jun. 1964.
Chem. Abst. 119: 272511 of DE 4,232,213.

*Primary Examiner*—Mark Chapman
*Attorney, Agent, or Firm*—David R. Crichton

[57] ABSTRACT

Novel (cyclo)aliphatic epoxy compounds that contain at least one acrylate group in the molecule and at least one cycloaliphatic epoxy group can be used for the production of coating formulations, adhesives, photoresists or in stereolithography. As they contain a cohesive homogeneous network, the three-dimensional objects produced have very good green strength and very good strength properties.

6 Claims, No Drawings

(CYCLO)ALIPHATIC EPOXY COMPOUNDS

This is a division of Ser. No. 08/169,938, filed Dec. 20, 1993 now U.S. Pat. No. 5,468,886.

The present invention relates to novel (cyclo)aliphatic epoxy compounds, to their preparation and to methods of polymerising these compounds by actinic radiation, to their use in stereolithography for the production of three-dimensional objects, as well as to the use of said novel (cyclo)aliphatic epoxy compounds as adhesives, coating compositions and resists.

It is common knowledge that radiation-sensitive resins or resin mixtures have versatile utilities, typically as coating formulations, adhesives or photoresists. Quite generally, these resins or resin systems should also be suitable for the production of three-dimensional objects (3D objects) by the stereolithographic technique disclosed in U.S. Pat. No. 4,575,330. However, many resins prove to be too viscous, whereas others are too insufficiently light-sensitive or suffer too severe shrinkage during the cure. The strength properties of the moulder articles or objects fabricated from photocured resins are also often unsatisfactory.

That complicated three-dimensional objects can be formed from liquid light-sensitive resins by the stereolithographic technique is well-known. Such objects are formed from layers by bonding each new curable resin layer tenaciously to the previously prehardened layer by curing with UV/VIS light. It is common knowledge that the total assembly of the three-dimensional object can be accomplished by means of a computer-controlled process.

In recent years there has been no lack of efforts to develop resin systems suitable for the technique of stereolithography. In Rev. Sci. Instrum. 52 (11) 1170–1173 (1981), H. Kodama discloses under the registered trademark "Tevista" a liquid photohardening resin formulation comprising an unsaturated polyester, acrylate, styrene, a polymerisation initiator and a sensitiser. The drawback of this resin system for use in stereolithography is that the photosensitivity is insufficient and the so-called "green strength" of the objects hardened by laser beams is rather low.

A stereolithographic technique is described in U.S. Pat. No. 4,575,330 in which the liquid resin used is a modified acrylate which is referred to in the description as "Potting Compound 363". Such resin formulations are disclosed in U.S. Pat. No. 4,100,141. They too have the drawback of being insufficiently light-sensitive and of requiring lengthy times for the fabrication of three-dimensional objects by the stereolithographic technique.

It is therefore understandable that the demands made of resins for use in stereolithography are high. For example, the photosensitivity of the resin system must be such that the ratio of the radiation energy applied and the depth of penetration into the liquid photosensitive resin formulation so as to effect solidification of the parts is within reasonable limits. This means that, when using a resin suitable for use in stereolithography, the aim shall be to achieve the greatest possible curing depth with little radiation energy, simultaneously coupled with a high degree of polymerisation and good green strength.

In the technique employed in stereolithography of successively polymerising thin layers, none of the layers is usually fully cured. The incompletely cured object is called a "green model", and the module of elasticity and the tensile strength of this green model is called the green strength. Normally the green model is cured with UV/VIS light, conveniently with a mercury or xenon arc lamp. The green strength of an object is therefore an important parameter, as objects having a low green strength may become deformed under their own weight or, in the course of the cure, they may sag or collapse.

To obtain useful compounds especially for stereolithography, the prior an also postulates mixtures of acrylate compounds with epoxy resins, inter alia also in EP-A-0 360 869. These mixtures, however, have the drawback that the final products fabricated from them are brittle. Moreover, during the cure two independent networks form, resulting in a detrimental effect on the green strength.

Finally, EP patent application 0 485 990 discloses heat-curable formulations that contain acrylic polymers having functional alicyclic epoxy groups.

Accordingly, it is the object of the present invention to provide compounds that overcome the drawbacks discussed above. i.e. compounds having the right viscosity and light-sensitivity for stereolithographic utilities and containing no independent network, but a cohesive homogeneous network so that the green strength and strength properties of the three-dimensional objects produced are generally enhanced.

This object is achieved with a novel class of (cyclo)aliphatic epoxy compounds. These compounds contain in one and the same molecule at least one acrylate and one epoxy group, preferably two or also more such groups, and hence constitute multifunctional compounds. Such compounds are not known and disclosed in the prior art.

It is surprising that, on the one hand, such molecules can be prepared with relative ease and that they readily polymerise radically and/or cationically, and, on the other, that these compounds may suitably be used in stereolithography. A cohesive homogeneous network is thereby obtained, affording in particular advantages for the green strength.

Irradiation of the formulations prepared from these novel (cyclo)aliphatic epoxy compounds thus makes it possible to achieve different crosslinking densities, so that the green models formed during the precure by laser irradiation as well as the objects obtained by curing the green models have good properties, in particular good strength properties, that are capable of variation within wide limits.

Specifically, the invention relates to novel (cyclo)aliphatic epoxy compounds of formulae

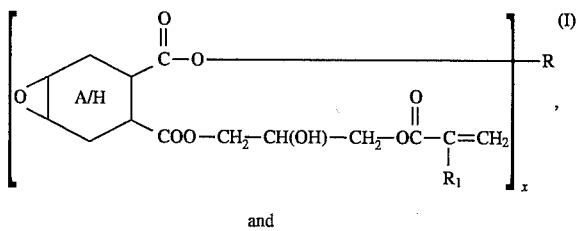

and

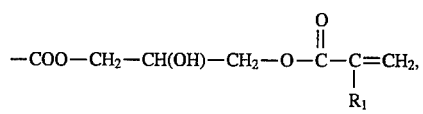

wherein a is a radical of formula $$-COO-CH_2-CH(OH)-CH_2-O-\overset{\overset{O}{\|}}{C}-\underset{\underset{R_1}{|}}{C}=CH_2,$$

A is a cyclohexyl radical or a hydrogenated radical of formula

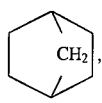

R is a radical of formula $(-CH_2)_yCH_3$, $(-CH_2-)_y$,

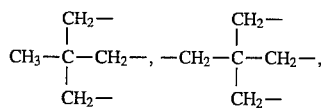

an unsubstituted or substituted monovalent to hexavalent aliphatic alcohol radical, an unsubstituted or substituted aromatic-aliphatic alcohol radical, an unsubstituted or substituted monovalent to tetravalent polyether rest or polyester radical, an unsubstituted or substituted monovalent to tetravalent polycaprolactone radical, an unsubstituted or substituted monovalent to tetravalent polyurethane radical or a radical of formula

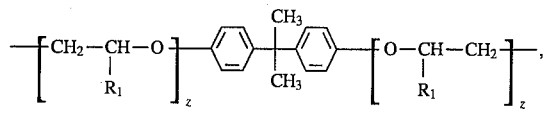

and $R_1$ is hydrogen or $CH_3$, x is an integer from 1 to 6, y is an integer from 2 to 20 z is an integer from 1 to 10, and $R_3$ and $R_4$ are each independently of the other an unsubstituted or substituted aliphatic, aromatic or cycloaliphatic hydrocarbon radical.

Compounds of formula I are preferred, more particularly those in which A is a cyclohexyl radical, a R $[-CH_2-]_y$ group or a radical of formula

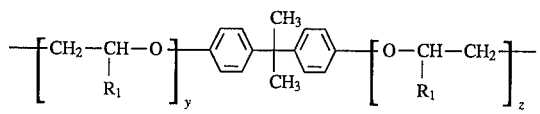

where y, z and $R_1$ are as defined in claim 1, and x is 2.

The alkyl or alkylene radicals $(-CH_2)_yCH_3$ or $(-CH_2-)_y$ represented by R may be straight-chain or branched and are typically methyl, ethyl, n-propyl, isopropyl, n-butyl, sec-butyl, tert-butyl, pentyl, hexyl, heptyl, octyl, nonyl, decyl, undedyl, dodecyl, tetradecyl, hexadecyl, icosyl or docosyl, and the corresponding alkylene radicals.

R defined as an unsubstituted or substituted monovalent to hexavalent aliphatic alcohol radical may suitably be in particular a radical of the following compounds: aliphatic diols, such as ethylene glycol, 1,2-propanediol, 1,3-propanediol, 1,4-butanediol, 1,5-pentanediol, neopentyl glycol, 1,6-hexanediol, 1,8-octanediol, 1,10-decanediol or 1,12-dodecanediol; cycloaliphatic diols such as 1,3- or 1,4-dihydroxycyclohexane, 1,4-cyclohexanedimethanol, bis(4-hydroxycyclohexyl)methane or 2,2-bis(4-hydroxycyclohexyl)propane. Illustrative examples of higher functional alcohols are 1,1,1-trimethylolethane, 1,1,1-trimethylolpropane, glycerol, pentaerythritol or 1,3,5-trihydroxybenzene.

R defined as an unsubstituted or substituted aromatic-aliphatic alcohol radical may typically be a radical of the following compounds: benzyl alcohol, phenylethyl alcohol, phenylpropyl alcohol and the compound of formula

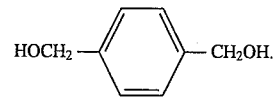

R defined as an unsubstituted or substituted monovalent to tetravalent polyether radical is preferably selected from the following radicals:

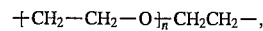

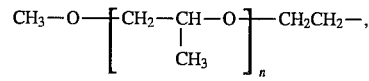

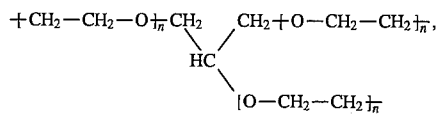

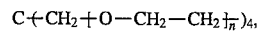

in which n is an integer from 1 to 20, or

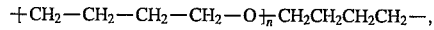

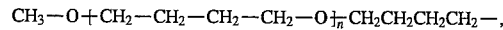

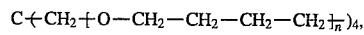

in which n is an integer from 1 to 20.

R defined as an unsubstituted or substituted monovalent to tetravalent polyester radical may typically be a radical selected from:

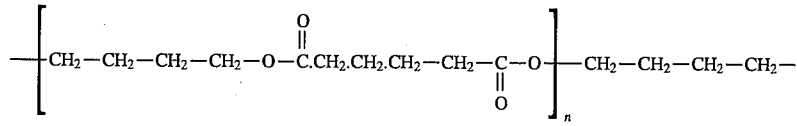

and

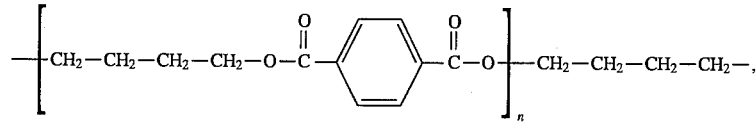

in which n is an integer from 1 to 20.

R defined as an unsubstituted or substituted monovalent to tetravalent polycaprolactone radical is selected from

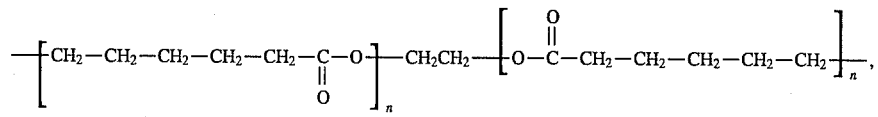

and

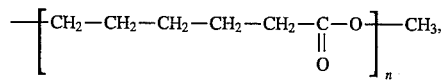

in which n is an integer from 1 to 20.

R defined as an unsubstituted or substituted monovalent to tetravalent polyurethane is selected from the following radicals:

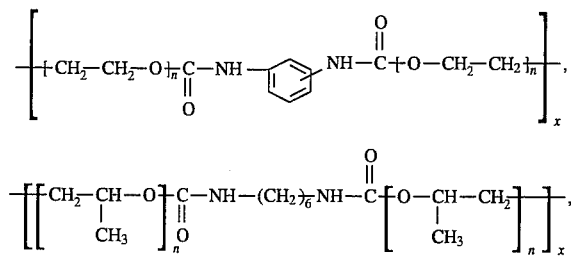

wherein n is an integer from 1 to 20 and x is an integer from 1 to 10.

$R_3$ and $R_4$ as an unsubstituted or substituted aliphatic hydrocarbon radical, is preferably a straight-chain or branched $C_1$–$C_{20}$ alkyl radical which may carry one or more substituents, typically halogen such as F, Cl or Br, or $NO_2$, CN or aryl such as phenyl, and which may also be interrupted by ester or ether groups. Such radicals are typically the following:

—$(CH_2)_2$—, —$(CH_2)_6$—, isopropyl, isobutyl or also a (poly)ether or (poly)ester radical, typically

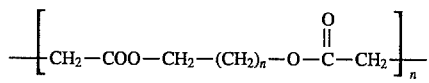

or

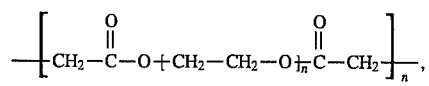

wherein n is an integer from 1 to 20.

$R_3$ and $R_4$ defined as an unsubstituted or substituted aromatic hydrocarbon radical is typically a phenyl or naphthyl radical which may be substituted by a $C_1$–$C_{20}$ alkyl radical, which alkyl radical may carry one or more further substituents selected from the group consisting of halogen such as F, Cl or Br, and $NO_2$, CN and aryl, e.g. phenyl, and which alkyl radical may also be interrupted by ester or ether groups. Typical radicals of this kind are the following:

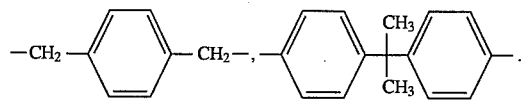

$R_3$ and $R_4$ defined as an unsubstituted or substituted cycloaliphatic hydrocarbon radical may typically be a cycloaliphatic 5-, 6- or 7-membered ring which may be

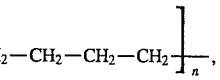

substituted by a $C_1$–$C_{20}$ alkyl radical, which alkyl radical may carry one or more further substituents selected from the group consisting of halogen such as F, Cl or Br, and $NO_2$, CN and aryl, e.g. phenyl, and may also be interrupted by ester or ether groups. Typical radicals of this kind are the following:

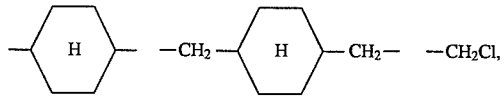

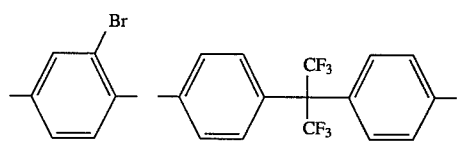

Usually, and depending on the nature of the radicals R, $R_3$ und $R_4$, the novel (cyclo)aliphatic epoxy compounds are low- to high-viscosity resins which dissolve readily in organic solvents such as toluene, ethyl acetate, tetrahydrofuran as well as in other polymerisable monomers such as (meth)acrylates or epoxides.

The (cyclo)aliphatic epoxy compounds of formula I can be prepared in a manner known per se, conveniently by reacting at least 1 mol of a cyclic unsaturated anhydride of formula III

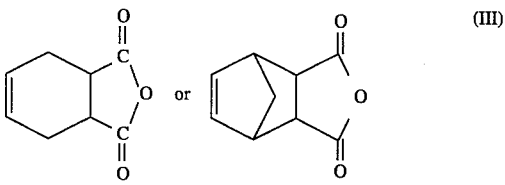

(III)

with at least 1 mol of a compound that introduces the radical R to give a diester-dicarboxylic acid of formula IV

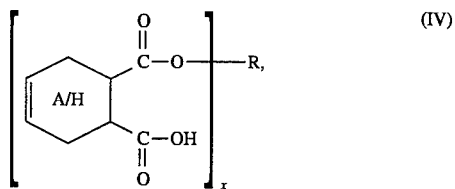

(IV)

which is then further reacted with glycidyl (meth)acrylate to the product of formula V

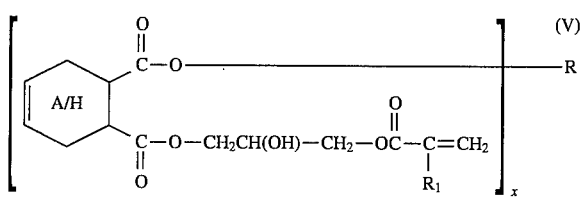

which is in turn subsequently oxidised to the (cyclo)aliphatic epoxy compound of formula I, or, to prepare compounds of formula II, oxidising corresponding unsaturated carboxyl group containing and (meth)acrylate group containing compounds.

Compounds that introduce the group R are suitably those which contain at least one hydroxyl group, typically 1,4-butanediol, 1,6-hexanediol, diethylene glycol and polyethylene glycols. The reaction of the anhydride of formula (III) with the compound that introduces the radical R is preferably carried out in the temperature range from 90° C. to 130° C. in the absence or presence of a catalyst such as N,N-dimethylbenzylamine, and with or without an inert organic solvent. The diester-dicarboxylic acid formula IV so obtained need not be isolated. It is then reacted with glycidyl acrylate/methacrylate in the presence of an inhibitor (e.g. di-tert-butyl-p-cresol) to the acrylate (V), which is subsequently oxidised in the temperature range from 15° C. to at most 40° C. The oxidation is carried out with a solution of peracetic acid in acetic acid in the absence or presence of a chlorinated hydrocarbon such as chloroform or, preferably, methylene chloride.

The open-chain (cyclo)aliphatic epoxy compounds of formula II can be prepared from unsaturated carboxyl group containing compounds by reacting the carboxyl groups with glycidyl (meth)acrylate and subsequently oxidising the double bonds. Suitable carboxyl group containing compounds are unsaturated dicarboxylic acids or unsaturated polyethers or polyesters carrying acid end groups.

The novel inventive (cyclo)aliphatic epoxy compounds can be further processed with a wide range of components for preparing formulations. Such formulations comprise a) 5 to 99% by weight of a (cyclo)aliphatic epoxy compound of formula I or II, and b) 0 to 10% by weight of a radical photoinitiator.

Typical known photoinitiators are benzoins, including benzoin, benzoin ethers such as benzoin methyl ether, benzoin ethyl ether and benzoin isopropyl ether, benzoin phenyl ether and benzoin acetate, acetophenones, including acetophenone, 2,2-dimethoxyacetophenone and 1,1-dichloroacetophenone, benzil, benzil ketals, such as benzil dimethyl ketal and benzil diethyl ketal, anthraquinones, including 2-methylanthraquinone, 2-ethylanthraquinone, 2-tert-butylanthraquinone, 1-chloroanthraquinone and 2-amylanthraquinone, triphenylphosphine, benzoylphosphine oxides, for example 2,4,6-trimethylbenzoyldiphenylphosphine oxide (Luzirin TPO), benzophenones, such as benzophenone and 4,4'-bis-(N,N'-dimethylamino)benzophenone, thioxanthones and xanthones, acridine derivatives, phenazine derivatives, quinoxaline derivatives or 1-phenyl-1,2-propanedione, 2-O-benzoyl oxime, 1-aminophenyl ketones or α-hydroxy-phenyl ketones, such as 1-hydroxycyclohexyl phenyl ketone, phenyl 1-hydroxyisopropyl ketone and 4-isopropylphenyl 1-hydroxyisopropyl ketone, all of which are known compounds.

Particularly suitable photoinitiators which are normally used in conjunction with a HeCd laser as radiation source are acetophenones, conveniently 2,2-dialkoxybenzophenones and α-hydroxy-phenyl ketones, for example 1-hydroxycyclohexyl phenyl ketone or 2-hydroxyisopropyl phenyl ketone (=2-hydroxy-2,2-dimethylacetophenone).

Another class of photoinitiators which are normally employed when irradiating with argon ion lasers are the benzil ketals, typically benzil dimethyl ketal.

Another class of suitable photoinitiators comprises the ionic dye-counter ion compounds which are capable of absorbing actinic radiation and generating free radicals which are able to initiate the polymerisation of the epoxy compounds. The novel formulations containing ionic dye-counter ion compounds can be cured more variably in this way with visible light within the adjustable wavelength range of 400–700 nm. Ionic dye-counter ion compounds and their mode of action are known, for example from EP-A-0 223 587 and U.S. Pat. Nos. 4,751,102; 4,772,530 and 4,772,541. Typical examples of suitable ionic dye-counter ion compounds are the anionic dye-iodonium ion complexes, the anionic dye-pyrylium ion complexes and, especially, the cationic dye-borate anion compounds of formula

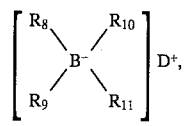

wherein $D^+$ is a cationic dye and $R_8$, $R_9$, $R_{10}$ and $R_{11}$ are each independently of one another alkyl, aryl, alkaryl, allyl, aralkyl, alkenyl, alkynyl, an alicyclic or saturated or unsaturated heterocyclic group. Preferred definitions of the substituents $R_8$ to $R_{11}$ will be found in EP-A-223 587.

It is common practice to add the photoinitiators in effective amounts, i.e. in amounts of about 0.1 to 10% by weight, based on the total mount of the formulation. If the novel formulations are used for stereolithographic methods in which laser beams are normally used, it is essential to adjust the absorption capacity of the mixtures by the type and concentration of the photoinitiator such that the depth of cure at normal laser speed is about 0.1 to 2.5 mm.

Further suitable photoinitiators may also be compounds of different sensitivity to radiation of emission lines of different wavelengths. The inclusion of such photoinitiators effects the better utilisation of a UV/VIS light source which radiates emission lines of different wavelength. It is advantageous to choose the different photoinitiators and to use them in such concentration that a uniform optical absorption is produced with respect to the emission lines used.

The preferred photoinitiator is an α-hydroxy-phenyl ketone, and 1-hydroxycyclohexyl phenyl ketone is particularly preferred.

The above described formulations can additionally contain further components:

c) 0 to 20% by weight of customary additives, typically stabilisers such as UV stabilisers, polymerisation inhibitors, slip agents, wetting agents, flow control agents, sensitisers, antiprecipitants, surfactants, dyes, pigments or fillers;

d) 0 to 80% by weight of a mono-, di- or polyfunctional (meth)acrylate, typically mono(meth)acrylate, mono-N-vinyl compounds having a maximum MW 500, aliphatic or cycloaliphatic di(meth)acrylates, aliphatic tri(meth)acrylates or aromatic di- or tri(meth)acrylates;

e) 0 to 80% by weight of a di- or polyfunctional customary aromatic, alicyclic or aliphatic epoxy resin. Epoxy resins suitable for use in the formulations of this invention are disclosed in EP-A-0 360 869. It is preferred to use butanediol diglycidyl ether and 3,4-epoxycyclohexyl-3',4'-epoxycyclohexanecarboxylate.

f) 0 to 50% by weight of a OH-terminated polyether or polyester, typically a di- or trifunctional polyether or polyester-polyol, polytetrahydrofuran, poly-ε-caprolactone and a OH-terminated polyurethane. OH-Terminated polycaprolactone is of particular interest;

g) 0.5 to 5% by weight of a cationic photoinitiator, as described in EP-A-0 360 869. Triarylhexafluoroantimonate, for example triarylsulfonium hexafluoroantimonate, is of particular interest.

Preferred formulations comprise
a) 5 to 60% by weight of a (cyclo)aliphatic epoxy compound of formula I or II,
b) 0 to 10% by weight of a radical photoinitiator,
c) 0 to 10% by weight of customary additives,
d) 0 to 40% by weight of a mono-, di- or polyfunctional (meth)acrylate,
e) 30 to 70% by weight of a di- or polyfunctional epoxide,
f) 5 to 40% by weight of a OH-terminated polyether or polyester, and
g) 0.5 to 5% by weight of a cationic photoinitiator.

The formulations suitable for use in the practice of this invention can be prepared in known manner, conveniently by premixing individual components and subsequently blending these premixes, or by blending all components in conventional apparatus, such as stirred vessels, preferably excluding light and at ambient or slightly elevated temperature, typically in the range from c. 50° C. to 70° C.

The formulations suitable for use in the practice of this invention containing the novel (cyclo)aliphatic epoxy compounds can be polymerised by irradiation with actinic light, typically with electron beams or X-rays, UV or VIS light, i.e. with electromagnetic or particle radiation in the wavelength range from 280–650 nm. Particularly suitable light sources are HeCd, argon or nitrogen laser light as well as metal vapour and NdYAG lasers with multiple frequency. Those skilled in the art will know that the appropriate photoinitiator for each selected light source must be chosen and, if necessary, sensitised. It has been found that the depth of penetration of the radiation into the polymerised formulation and the processing rate are directly related to the absorption coefficient and the concentration of the photoinitiator. In stereolithography it is preferred to use those photoinitiators which generate the highest number of resulting free radicals and make possible the greatest depth of penentration into the formulations to be polymerised.

Accordingly, the invention also relates to a process for polymerising the novel formulations by irradiating said formulations with actinic light. The resultant polymers may be used conveniently as coating compounds, photoresists or adhesives.

The invention further relates to a process for the production of three-dimensional objects from a novel liquid formulation by lithographic techniques, especially by stereolithography, which comprises irradiating a layer of novel liquid formulation over the entire surface or in a predetermined pattern with a UV/VIS light source, such that within the irradiated areas a layer solidifies in a desired layer thickness, then forming a new layer of novel formulation on the solidified layer, which is likewise irradiated over the entire surface or in a predetermined pattern, and such that three-dimensional objects are formed from a plurality of solidified layers which adhere to one another by repeated coating and irradiation.

In this process it is preferred to use a laser light which is computer-controlled in a particularly preferred embodiment of the invention.

If the novel formulations are used as coating compounds, clear and hard coats are obtained on wood, paper, metal, ceramic or other surfaces. The coating thickness can vary greatly over a very wide range and be from c. 1 μm to c. 1 mm. Relief images for printed circuit boards or printing plates can be produced from the novel formulations, conveniently by computer-controlled laser light of appropriate wavelength or using a photomask and a suitable light source.

A further utility of the novel formulations is as photocurable adhesives. It is preferred to use the novel formulations for the production of photopolymerised layers, especially in the form of three-dimensional objects which are formed from a plurality of solidified layers which adhere to one another.

The following non-limitative Examples illustrate the invention in more detail.

EXAMPLE 1

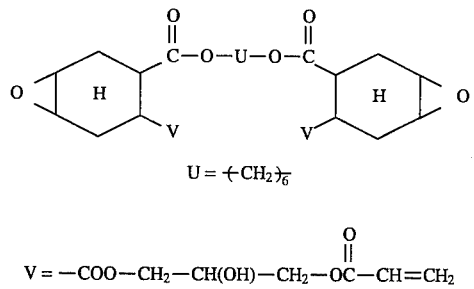

$U = -(CH_2)_6-$ $V = -COO-CH_2-CH(OH)-CH_2-OC(=O)-CH=CH_2$ 76.07 g (0.5 mol) of tetrahydrophthalic anhydride are fused at 110° C. in a sulfonating flask fitted with stirrer, reflux condenser and thermometer. Then 0.67 g of N,N-dimethylbenzylamine and 59.09 g (0.25 mol) of 1,6-hexanediol are added with stirring. The mixture is stirred for 3 h at 110° C.

To the diester-dicarboxylic acid so obtained is added 0.27 g of di-tert-butyl-p-cresol. A mixture of 64.06 g (0.5 mol) of glycidyl acrylate, 0.24 g (0.12%) of Nuosyn Chromium® (fatty acid chromium salt in hydrocarbons, supplied by Durham Chemicals, Durham, GB) and 0.13 g of di-tert-butyl-p-cresol is then added dropwise. The mixture is further stirred at 110° C. until the epoxy value is <0.05 eq/kg (c. 18 h).

180 g of the unsaturated diacrylate so obtained are dissolved in 300 ml of methylene chloride at room temperature and then 15 g of sodium acetate are added, followed by the dropwise addition of 141.18 g (0.74 mol) of 40% peracetic acid in acetic acid, while ensuring that the temperature does not exceed 40° C. Stirring is continued for a further 5 h at 35° C.

The solution is thereafter extracted with 5% aqueous NaHCO$_3$ and then with water. The organic phase is dried and, after destroying the peroxides with (with sodium sulfite), concentrated by evaporation under vacuum.

Yield: 142 g (75%) of the product of the above formula in the form of a colourless viscous resin having a viscosity of η (20° C.)>10 000 mPa.sec.

Epoxy value: 1.51 eq/kg (54% of theory).

EXAMPLE 2

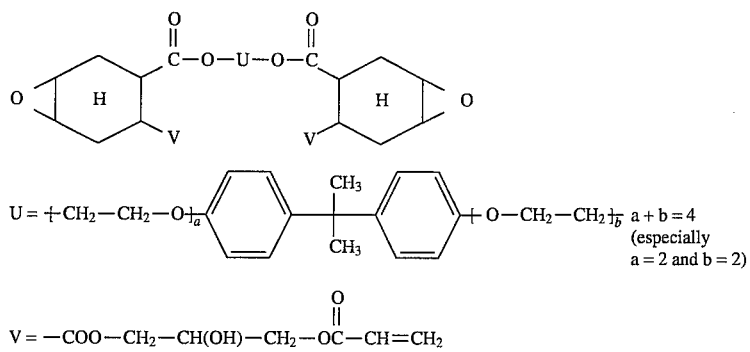

76.07 g (0.5 mol) of tetrahydrophthalic anhydride are reacted with 245.84 g (0.25 mol) of Dianol 2211 (aliphatic-aromatic dialcohol sold by Akzo Chemie; its chemical formula corresponds to formula U above with additionally two terminal hydroxyl groups) by the method described in Example 1.

A mixture of 64.06 g (0.5 mol) of glycidyl acrylate, 0.24 g (0.12%) of Nuosyn Chromium® and 0.48 g (0.2%) of di-tert-butyl-p-cresol is added dropwise to the diester-dicarboxylic acid so obtained. After a reaction time of c. 5 h the epoxy value is <0.06 eq/kg.

Following the procedure described in Example 1,200 g (0.207 mol) of the resultant unsaturated diacrylate are oxidised with 110 g (0.58 mol) of 40% peracetic acid in acetic acid.

Yield: 201.8 g (88%) of the product of the above formula in the form of a yellowish viscous resin.

Epoxy value: 1.07 eq/kg (54% of theory).

EXAMPLE 3

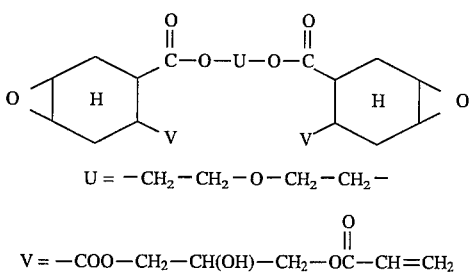

76.07 g (0.5 mol) of tetrahydrophthalic anhydride are reacted with 25.5 g (0.25 mol) of diethylene glycol in accordance with the method described in Example 1. A mixture of 64.06 g (0.5 mol) of glycidyl acrylate, 0.2 g (0.12%) of Nuosyn Chromium® and 0.33 g (0.2%) of di-tert-butyl-p-cresol is added dropwise to the diester-dicarboxylic acid so obtained. After a reaction time of c. 5 h the epoxy value is <0.05 eq/kg.

Following the procedure described in Example 1, 50 g (0.075 mol) of the resultant unsaturated diacrylate are oxidised with 39.9 g (0.21 mol) of peracetic acid.

Yield: 40 g (74.4%) of the product of the above formula in the form of a colourless viscous resin.

Epoxy value: 1.89 eq/kg (70.8% of theory).

EXAMPLE 4

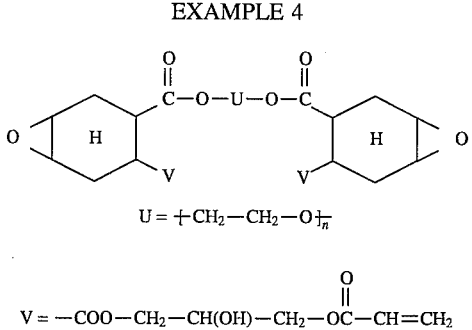

76.07 g (0.5 mol) of tetrahydrophthalic anhydride are reacted with 150 g (0.25 mol) of polyethylene glycol 600 (n~14) in accordance with the method described in Example 1. A mixture of 64.06 g (0.5 mol) of glycidyl acrylate, 0.24 g (0.12%) of Nuosyn Chromium® and 0.58 g (0.2%) of di-tert-butyl-p-cresol is added dropwise to the diester-dicarboxylic acid so obtained. After a reaction time of c. 5 h at 120° C. the epoxy value is <0.05 eq/kg.

Following the procedure described in Example 1, 54.27 g (0.045 mol) of the resultant unsaturated diacrylate are oxidised with 23.75 g (0.125 mol) of 40% peracetic acid in acetic acid.

Yield: 50 g (90.8%) of the product of the above formula in the form of a colourless viscous resin having a viscosity of η=10 000 mPa.sec (35° C.).

Epoxy value: 0.76 eq/kg (46.2% of theory).

EXAMPLE 5

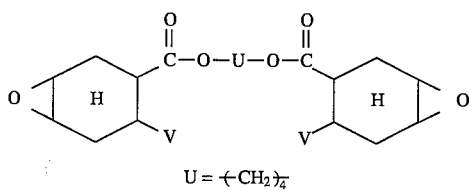

76.07 g (0.5 mol) of tetrahydrophthalic anhydride are reacted with 22.53 g (0.25 mol) of butanediol in accordance with the method described in Example 1.

A mixture of 64.06 g (0.5 mol) of glycidyl acrylate, 0.2 g (0.12%) of Nuosyn Chromium® and 0.33 g (0.2%) of di-tert-butyl-p-cresol is added dropwise to the diester-dicarboxylic acid so obtained. After a reaction time of c. 10 h the epoxy value is <0.06 eq/kg.

Following the procedure described in Example 1, 70 g (0.11 mol) of the resultant unsaturated diacrylate are oxidised with 59.6 g (0.31 mol) of 40% peracetic acid in acetic acid.

Yield: 56 g (78%) of a colourless viscous resin of the above formula.

Epoxy value: 2.19 eq/kg (71.8% of theory).

EXAMPLE 6

$$V-(CH_2)_6-\underset{\underset{O}{\diagdown\diagup}}{\overset{CH_3}{\underset{|}{C}}}-CH-(CH_2)_2-CH-\underset{\underset{O}{\diagdown\diagup}}{\overset{CH_3}{\underset{|}{C}}}-(CH_2)_6-V$$

in which $$V = -COO-CH_2-CH(OH)-CH_2-O\overset{O}{\underset{||}{C}}-CH=CH_2$$

60 g (0.096 mol) of a product obtained by reacting IPU 22-G® (unsaturated long-chain diepoxide sold by Okamura Oil Mill, Japan) with 2 equivalents of acrylic acid are oxidised as described in Example 1 with 51.3 g (0.27 mol) of 40% peracetic acid in acetic acid.

Yield: 59.6 g (95%) of the product of the above formula in the form of a colourless viscous resin.

Epoxy value: 1.1 eq/kg (36% of theory).

EXAMPLE 7

$$W\!-\!\!\left[\!-\!O\!-\!\overset{O}{\underset{||}{C}}\!-\!CH_2\!-\!\underset{\underset{O}{\diagdown\diagup}}{CH}\!-\!CH\!-\!CH_2\!-\!\overset{O}{\underset{||}{C}}\!-\!O\!-\!(CH_2)_4\!-\!\right]_n\!\!-\!W_1,$$

wherein $$W = -CH_2-CH(OH)-CH_2-O\overset{O}{\underset{||}{C}}-CH=CH_2$$

and $$W_1-\overset{O}{\underset{||}{C}}O-CH_2-\underset{\underset{O}{\diagdown\diagup}}{CH}-CH-CH_2-COO-CH_2-CH(OH)-CH_2-O\overset{O}{\underset{||}{C}}-CH=CH_2$$

50 g (0.35 mol) of trans-3-hexenedicarboxylic acid and 15.6 g (0.17 mol) of butanediol are suspended in 100 ml of toluene. After addition of 0.65 g of p-toluenesulfonic acid, the mixture is heated to 120° C., while removing the water of reaction with a water separator. After c. 5 h the removal of water is complete (5.7 ml, theory 6.3 ml). The crystalline precipitate that forms during cooling is isolated by filtration and recrystallised from tetrahydrofuran.

Yield: 28.7 g (49.3%).

A mixture of 21.16 g (0.165 mol) of glycidyl acrylate, 0.06 g of Nuosyn Chromium® and 0.1 g (0.2%) of di-tert-butyl-p-cresol is added dropwise to 28.26 g (0.0825 mol) of the acid polyester so obtained. After a reaction time of 12 h the epoxy value is <0.06 eq/kg. Following the procedure described in Example 1,30 g (0.05 mol) of the resultant unsaturated diacrylate are oxidised with 53.2 g (0.14 mol) of 20% peracetic acid in acetic acid, giving a colourless viscous resin of the above formula.

Epoxy value: 1.819 eq/kg (57% of theory).

EXAMPLE 8

$$O\underset{}{\underset{}{\bigtriangleup}}\underset{V}{\overset{\overset{O}{\underset{||}{C-O-U-O-C}}}{\underset{}{H}}}\underset{V}{\underset{}{\bigtriangleup}}O$$

$$U = -(-CH_2)_{12}-;$$

$$V = -COOCH_2-CH(OH)-CH_2-O-\overset{O}{\underset{||}{C}}-\underset{\underset{CH_3}{|}}{C}=CH_2$$

76.07 g (0.5 mol) of tetrahydrophthalic anhydride are reacted with 50.59 g (0.25 mol) of 1,2-dodecanediol in accordance with the method described in Example 1.

A mixture of 71.08 g (0.5 mol) of glycidyl acrylate, 0.24 g (0.12%) of Nuosyn Chromium® and 0.40 g (0.2%) of di-tert-butyl-p-cresol is added dropwise to the diester-dicarboxylic acid so obtained. After a reaction time of 7.5 h, a product with an epoxy value of <0.05 eq/kg is obtained.

Following the procedure described in Example 1, 199.02 g (0.025 mol) of the resultant unsaturated dimethacrylate are oxidised with 133.09 g (0.70 mol) of 40% peracetic acid in acetic acid.

Yield: 201.6 g (98.2%) of the product of the above formula in the form of a brown viscous resin.

Epoxy value: 1.28 eq/kg (52.5% of theory).

EXAMPLE 9

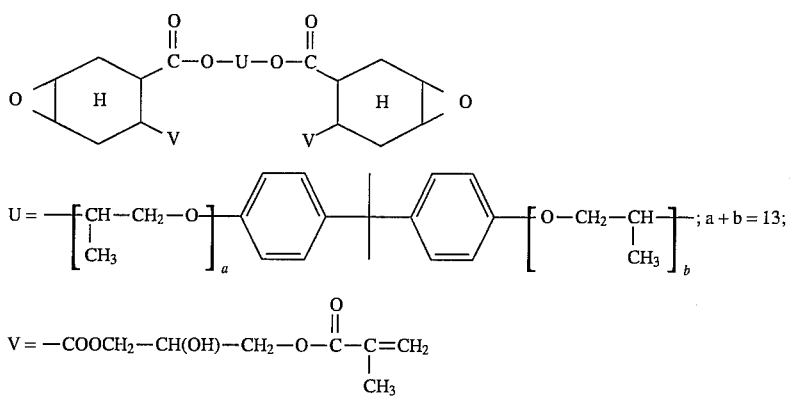

$U = -\left[\begin{array}{c}CH-CH_2-O\\|\\CH_3\end{array}\right]_a$ —⟨phenyl⟩—C(CH_3)_2—⟨phenyl⟩— $\left[O-CH_2-\begin{array}{c}CH\\|\\CH_3\end{array}\right]_b$—; a+b = 13;

$V = -COOCH_2-CH(OH)-CH_2-O-\underset{\underset{CH_3}{|}}{C}-C=CH_2$
$\phantom{V = -COOCH_2-CH(OH)-CH_2-O-}\overset{O}{\|}$ 76.07 g (0.5 mol) of tetrahydrophthalic anhydride are reacted with 245.84 g (0.25 mol) of Dianol® 3310 (aliphatic-aromatic dialcohol sold by Akzo Chemie; its chemical formula corresponds to formula U above with additionally two terminal hydroxyl groups) by the method described in Example 1.

A mixture of 71.08 g (0.5 mol) of glycidyl methacrylate, 0.47 g (0.12%) of Nuosyn Chromium® and 0.79 g (0.2%) of di-tert-butyl-p-cresol is added dropwise to the diester-dicarboxylic acid so obtained. After a reaction time of c. 5.5 h, a product with an epoxy value of <0.07 eq/kg is obtained.

Following the procedure described in Example 1,395 g (0.26 mol) of the resultant unsaturated diacrylate are oxidised with 136.89 g (0.72 mol) of 40% peracetic acid in acetic acid.

Yield: 383.5 g (93.6%) of the product of the above formula in the form of a brown oil.

Epoxy value: 0.72 eq/kg (56.7% of theory).

EXAMPLE 10

Preparation of the formulations:

All components listed a) to d) below are mixed at 60° C. in a round-bottomed flask until a homogeneous solution forms. The viscosities of these solutions are measured at 30° C. The mechanical properties of the formulations obtained are determined by testing three-dimensional objects produced with He/Cd lasers, viz. directly after laser curing as well as after the full cure (30 minutes with UV light, 30 minutes at 130° C.).

The curl factor (CF) is a value used in stereolithography for comparing the shrinkage phenomena of different mixtures with one another. Information regarding the determination of the CF will be found in the literature (e.g. Proceedings 2nd Int. Conference in Rapid Prototyping, Dayton, Ohio, 1991). The CF values reported here are determined by testing three-dimensional objects that have a layer thickness of 3 mils (0.076 mm).

a) The following components are mixed at 60° C. in a round-bottomed flask until a clear solution is obtained.
55.44 g of 3,4-epoxycyclohexyl-3,'4'-epoxycyclohexanecarboxylate,
18.55 g of butanediol diglycidyl ether,
13.1 g of a trifunctional OH-terminated polycaprolactone, Union Carbide,
1–2.1 g of the product of Example 1,
0.6 g of 1-hydroxycyclohexyl phenyl ketone, and
0.6 g of triarylsulfonium hexafluoroantimonate (Union Carbide; aryl is principally phenyl).

The viscosity of this mixture is 97.2 mPa.sec (30° C.).

Three-dimensional objects are produced with a He/Cd laser (320 mJ/cm2). Directly after the laser cure (green models), these objects have the following properties: modulus of electricity=828N/mm2 and elongation at break=5%.

To effect the full cure, the green models are irradiated for 30 minutes with UV/VIS light and then treated for 30 minutes at 130° C. The objects then have the following properties:

modulus of elasticity: 748N/mm$^2$;
elongation at break: 22%.
The CF values are 0.01 for $CF_6$ and $CF_{11}$.

b) The following components are mixed at 60° C. until a homogeneous solution is obtained:
55.44 g of 3,4-epoxycyclohexyl-3,'4'-epoxycyclohexanecarboxylate,
18 g of butanediol diglycidyl ether,
13 g of a trifunctional OH-terminated polycaprolactone, Union Carbide,
12 g of the product of Example 2,
0.8 g of 1-hydroxycyclohexyl phenyl ketone, and
0.8 g of triarylsulfonium hexafluoroantimonate (Union Carbide).

The viscosity of this mixture is 235 mPa.sec (30° C.).

Directly after the laser cure (320 mJ/cm2), the three-dimensional objects produced have the following properties: modulus of electricity=338N/mm2 and elongation at break= 45%.

After the full cure (30 minutes with UV light, 30 minutes at 130° C.), the objects have the following properties:
modulus of elasticity: 1563N/mm$^2$;
elongation at break: 23%.
The CF values are 0.007 for $CF_6$ and 0.01 for $CF_{11}$.

c) The following components are mixed at 60° C. until a homogeneous solution is obtained:
55.44 g of 3,4-epoxycyclohexyl-3,'4'-epoxycyclohexanecarboxylate,
18 g of butanediol diglycidyl ether,
13 g of a trifunctional OH-terminated polycaprolactone, Union Carbide,
12 g of the product of Example 5,
0.8 g of 1-hydroxycyclohexyl phenyl ketone, and
0.8 g of triarylsulfonium hexafluoroantimonate (Union Carbide).

The viscosity of this mixture is 192 mPa.sec (30° C.).

Directly after the laser cure (640 mJ/cm2), the three-dimensional objects produced have the following properties: modulus of electricity=384N/mm2 and elongation at break=31%.

After the full cure (30 minutes with UV light, 30 minutes at 130° C.), the objects have the following properties:

modulus of elasticity: 1119N/mm$^2$;

elongation at break: 12.9%.

The curl factor of a three-dimensional object constructed by the weave style (q.v. for example Rapid Prototyping and Manufacturing, P. F. Jacobs ed., SME 1992, p. 199 et seq.) is 0.045 (CF$_6$).

d) The following components are mixed at 60° C. until a homogeneous solution is obtained:

47.4 g of 3,4-epoxycyclohexyl-3,'4'-epoxycyclohexanecarboxylate, 18 g of butanediol diglycidyl ether, 13 g of a trifunctional OH-terminated polycaprolactone, Union Carbide, 20 g of the product of Example 5, 0.8 g of 1-hydroxycyclohexyl phenyl ketone, and 0.8 g of triarylsulfonium hexafluoroantimonate (Union Carbide).

The viscosity of this mixture is 291 mPa.sec (30° C.).

After the laser cure (640 mJ/cm2), the three-dimensional objects produced have the following properties: modulus of electricity=68.8N/mm2 and elongation at break=39%.

After the full cure (30 minutes with UV light, 30 minutes at 130° C.), the objects have the following properties:

modulus of elasticity: 587N/mm$^2$;

elongation at break: 48%.

The curl factor of a three-dimensional object constructed by the weave style is 0.01.

What is claimed is:

1. A formulation comprising a) 5 to 60% by weight of a (cyclo)aliphatic epoxy compound of formula I or II $$\left[ O \underset{A/H}{\bigcirc} \overset{\overset{O}{\|}}{C} - O - R \atop COO-CH_2-CH(OH)-CH_2-O-\overset{\overset{O}{\|}}{C}-\underset{R_1}{C}=CH_2 \right]_x \quad (I)$$

and $$a-R_3-\underset{R_1}{\overset{|}{C}}\underset{O}{\diagdown\diagup}CH-R_4-HC\underset{O}{\diagdown\diagup}\underset{R_1}{\overset{|}{C}}-R_3-a, \quad (II)$$

wherein a is a radical of formula $$-COO-CH_2-CH(OH)-CH_2-O-\overset{\overset{O}{\|}}{C}-\underset{R_1}{C}=CH_2,$$

A is a cyclohexyl radical or a hydrogenated radical of formula $$\bigcirc\!\!\!\!\!\!\!\!\diagup CH_2,$$

R is a radical of formula (—CH$_2$)$_y$CH$_3$, (—CH$_2$—)$_y$, $$CH_3-\underset{\underset{CH_2-}{|}}{\overset{\overset{CH_2-}{|}}{C}}-CH_2-,\quad -CH_2-\underset{\underset{CH_2-}{|}}{\overset{\overset{CH_2-}{|}}{C}}-CH_2-,$$

an unsubstituted or substituted monovalent to hexavalent aliphatic alcohol radical, an unsubstituted or substituted aromatic-aliphatic alcohol radical, an unsubstituted or substituted monovalent to tetravalent polyether rest or polyester radical, an unsubstituted or substituted monovalent to tetravalent polycaprolactone radical, an unsubstituted or substituted monovalent to tetravalent polyurethane radical or a radical of formula $$\left[CH_2-\underset{R_1}{\overset{|}{CH}}-O\right]_z\!\!\!-\!\!\bigcirc\!\!-\!\!\underset{CH_3}{\overset{CH_3}{\underset{|}{C}}}\!\!-\!\!\bigcirc\!\!-\!\!\left[O-\underset{R_1}{\overset{|}{CH}}-CH_2\right]_z,$$

and

R$_1$ is hydrogen or CH$_3$, x is an integer from 1 to 6, y is an integer from 2 to 20, z is an integer from 1 to 10, and R$_3$ and R$_4$ are each independently of the other an unsubstituted or substituted aliphatic, aromatic or cycioaliphatic hydrocarbon radical, b) 0 to 10% by weight of a radical photoinitiator, c) 0 to 10% by weight of customary additives.

d) 0 to 40% by weight of a mono-, di- or polyfunctional (meth)acrylate, e) 30 to 70% by weight of a di- or polyfunctional epoxide, f) 5 to 40% by weight of a OH-terminated polyether or polyester, and g) 0.5 to 5% by weight of a cationic photoinitiator.

2. A formulation, containing a compound of formula I according to claim 1, wherein A is a (cyclohexyl) radical, a R[—CH$_2$—]$_y$ group or a radical of formula $$\left[CH_2-\underset{R_1}{\overset{|}{CH}}-O\right]_y\!\!\!-\!\!\bigcirc\!\!-\!\!\underset{CH_3}{\overset{CH_3}{\underset{|}{C}}}\!\!-\!\!\bigcirc\!\!-\!\!\left[O-\underset{R_1}{\overset{|}{CH}}-CH_2\right]_z,$$

where y, z and R$_1$ are as defined in claim 10 for formula I, and x is 2.

3. Use of a formulation as claimed in claim 1 for the production of coating compositions, adhesives, photoresists or for use in stereolithography.

4. A process for polymerising a formulation as claimed in claim 1, which comprises irradiating said formulation with actinic light.

5. A process for the production of a three-dimensional object from a formulation as claimed in claim 1 by a lithographic technique, which comprises irradiating a layer of said formulation over the entire surface or in a predetermined pattern with a UV and/or VIS light source, such that within the irradiated areas a layer solidifies in a desired layer thickness, then forming a new layer of said formulation on the solidified layer, which is likewise irradiated over the entire surface or in a predetermined pattern, and such that a three-dimensional object is formed from a plurality of solidified layers which adhere to one another by repeated coating and irradiation.

6. A process according to claim 5, wherein a laser beam, preferably a computer-controlled laser beam, is used as source of irradiation.

* * * * *